US012582508B2

(12) United States Patent
Liston et al.

(10) Patent No.: US 12,582,508 B2
(45) Date of Patent: Mar. 24, 2026

(54) OMNI-ABUTMENT CORE AND METHODS OF USE

(71) Applicant: ESTHETIC IMPLANT SOLUTIONS, LLC, Bountiful, UT (US)

(72) Inventors: Todd C. Liston, Pleasant View, UT (US); Mark H. Blaisdell, Bountiful, UT (US)

(73) Assignee: ESTHETIC IMPLANT SOLUTIONS, LLC, Bountiful, UT (US)

( * ) Notice: Subject to any disclaimer, the term of this patent is extended or adjusted under 35 U.S.C. 154(b) by 0 days.

(21) Appl. No.: 19/060,102

(22) Filed: Feb. 21, 2025

(65) Prior Publication Data

US 2025/0268694 A1     Aug. 28, 2025

Related U.S. Application Data

(60) Provisional application No. 63/710,443, filed on Oct. 22, 2024, provisional application No. 63/567,706, filed on Mar. 20, 2024, provisional application No. 63/557,379, filed on Feb. 23, 2024.

(51) Int. Cl.
| | |
|---|---|
| *A61C 8/00* | (2006.01) |
| *A61B 6/51* | (2024.01) |
| *A61B 90/00* | (2016.01) |

(52) U.S. Cl.
CPC ................ *A61C 8/005* (2013.01); *A61B 6/51* (2024.01); *A61C 8/0001* (2013.01); *A61C 8/008* (2013.01); *A61B 2090/3916* (2016.02)

(58) Field of Classification Search
CPC .............. A61C 8/00–0096; A61B 6/51; A61B 2090/3916
See application file for complete search history.

(56) References Cited

U.S. PATENT DOCUMENTS

| | | | |
|---|---|---|---|
| 5,810,592 A | * 9/1998 | Daftary ................. | A61C 8/008 |
| | | | 433/172 |
| 8,628,327 B1 | 1/2014 | Blaisdell et al. | |
| 9,572,640 B2 | 2/2017 | Blaisdell et al. | |
| | (Continued) | | |

OTHER PUBLICATIONS

International Search Report and Written Opinion for application No. PCT/US2025/016978 dated Apr. 17, 2025.

*Primary Examiner* — Yogesh P Patel
(74) *Attorney, Agent, or Firm* — Workman Nydegger

(57) ABSTRACT

An omni-abutment includes (i) an apical connection portion that mates/attaches with the receiving portion on a corresponding implant; and (ii) a coronal superstructure. The dental abutment provides features that are not currently found in abutments on the market, allowing the abutment to be used as a key foundation for scanning, impression taking, stability testing, and much more which ultimately would lead to an easier restorative process and fabrication of a dental prosthesis. The abutment could also be used for fabrication of a final prosthesis. The abutment may include alignment indents or protrusions in a platform thereof, internal grooves (e.g., square or rounded) as a tri-lobe or other configuration in the central axial hollow channel, recesses (e.g., divots, grooves) in the exterior periphery for increased adhesion to a gingival healing cuff, internal threading in the hollow channel, and a hex, NC or other connection at the apical connection portion.

21 Claims, 10 Drawing Sheets

(56)  References Cited

U.S. PATENT DOCUMENTS

| | | | |
|---|---|---|---|
| 9,895,209 B2 | 2/2018 | Blaisdell et al. | |
| 10,016,260 B2 | 7/2018 | Blaisdell et al. | |
| 10,470,856 B2 | 11/2019 | Liston et al. | |
| 10,507,081 B2 | 12/2019 | Blaisdell et al. | |
| 10,568,720 B2 | 2/2020 | Liston et al. | |
| 10,595,969 B2 | 3/2020 | Liston et al. | |
| 10,595,970 B2 | 3/2020 | Liston et al. | |
| 10,687,922 B2 | 6/2020 | Blaisdell et al. | |
| 10,695,152 B2 | 6/2020 | Liston et al. | |
| 10,709,525 B2 | 7/2020 | Liston et al. | |
| 11,253,345 B2 | 2/2022 | Liston et al. | |
| 11,478,339 B2 | 10/2022 | Liston et al. | |
| 11,559,379 B2 | 1/2023 | Liston et al. | |
| 11,571,283 B2 | 2/2023 | Liston et al. | |
| 12,245,916 B2 | 3/2025 | Liston et al. | |
| 2005/0287496 A1* | 12/2005 | Niznick | A61C 8/0066 433/173 |
| 2005/0287497 A1* | 12/2005 | Carter | A61C 8/005 433/173 |
| 2008/0166680 A1* | 7/2008 | Kast | A61C 8/005 433/37 |
| 2008/0206709 A1* | 8/2008 | Lannan | A61C 8/005 433/172 |
| 2012/0214130 A1* | 8/2012 | Krivoruk | A61C 13/0001 433/173 |
| 2013/0101964 A1* | 4/2013 | Fudim | A61C 8/006 433/214 |
| 2013/0177872 A1 | 7/2013 | Blaisdell et al. | |
| 2015/0004563 A1* | 1/2015 | Blaisdell | A61C 8/0001 433/173 |
| 2015/0104756 A1 | 4/2015 | Robb et al. | |
| 2018/0325631 A1 | 11/2018 | Christiansen et al. | |
| 2020/0375705 A1 | 12/2020 | Suttin et al. | |
| 2022/0151742 A1 | 5/2022 | Liston et al. | |
| 2022/0249206 A1 | 8/2022 | Liston et al. | |

* cited by examiner

202

202

202

200

200

200b

200b

OMNI-ABUTMENT CORE AND METHODS OF USE

CROSS-REFERENCE TO RELATED APPLICATIONS

This Application claims priority to and the benefit of U.S. Provisional Patent Application Ser. No. 63/557,379, filed Feb. 23, 2024, and titled "OMNI-ABUTMENT CORE AND METHODS OF USE," and Provisional Patent Application Ser. No. 63/710,443, filed Oct. 22, 2024, titled "3D PRINTED OR OTHER ANATOMICAL AND CIRCULAR GINGIVAL CUFFS", and Provisional Patent Application Ser. No. 63/567,706, filed Mar. 20, 2024, titled "CT SCANNING OF INTRAORAL SOFT TISSUE AND DENTAL STRUCTURES", each of which is herein incorporated by reference in its entirety.

Each of U.S. Pat. Nos. 8,628,327; 9,572,640; 9,895,209; 10,016,260; 10,687,922; 10,470,856; 10,595,969; 10,695,152; 10,507,081; 10,709,525; 11,253,345; 11,478,339; 10,595,970; 11,571,283; 10,568,720; and 11,559,379 and U.S. Publication Nos. 2022/0151742 and 2022/0249206, is each herein incorporated by reference in its entirety.

BACKGROUND OF THE INVENTION

1. The Field of the Invention

The present invention is in the field of dental abutments.

2. The Relevant Technology

While a variety of dental abutments are available within the art, including some configurations provided by applicant, there is still a continuing need for improved abutments that would provide additional features and functionality that is not currently available.

SUMMARY

An exemplary omni-abutment according to the present disclosure may include (i) an apical connection portion that would mate/attach with the receiving portion on a corresponding implant; and (ii) a coronal superstructure connection portion that serves as a core for attachment of a gingival healing cuff, where the coronal superstructure connection portion is connected to the apical connection portion either as one homogenous, seamless single piece of material or different biocompatible materials.

In an embodiment, at least a portion (e.g., the coronal superstructure) of the omni-abutment includes an irregular ovoid transverse cross-section, and/or a tri-lobe interior and/or exterior structure. In any case, the selected exterior configuration is not fully symmetrical, but is irregular in shape, which allows scanning of such structure in a way that allows the practitioner to determine orientation with certainty. For example, the abutment is not simply a hollow cylinder, as it is impossible to determine orientation of an abutment with such an exterior surface.

Also described is an omni-abutment and gingival healing cuff system, comprising an omni-abutment as described herein, and a gingival healing cuff that fits over the omni-abutment, wherein the gingival healing cuff may include corresponding structure for receipt of the exterior profile structure of the omni-abutment, so as to mate the two together in a keyed arrangement (e.g., rotation is not possible one relative to the other, once keyed).

In any of the described embodiments, the system may include a plurality of available gingival healing cuffs, each with a different size or configuration, wherein each cuff includes a hollow opening at a center portion of the gingival healing cuff, for receipt of the exterior profile structure of the omni-abutment. In an embodiment, the hollow opening in each gingival healing cuff is identically sized. In another embodiment, the hollow openings can be of different sizes, e.g., on cuffs that are of different shapes so they could fit over the abutments if they were of different diameters. By way of example, some commercially available implant screw heads are of different diameters. Differently sized hollow openings may be provided within a plurality of gingival healing cuffs to accommodate such.

In any of the described embodiments, the system may further comprise at least one of a buccal or lingual handle portion extending from the gingival healing cuff. In another embodiment, no handle(s) are provided.

In any of the described embodiments, at least one of the provided gingival healing cuffs may include a series of recessed dots or other markers in an exterior periphery of the gingival healing cuff, aligned with a lobe in the hollow opening of the gingival healing cuff. In another embodiment, no such dots or markers are provided. Such markers may similarly be provided in the omni-abutment, as well.

In any of the described embodiments, the omni-abutment may include something of a tri-lobe structure, either in a hollow axial channel of the coronal superstructure connection portion, or in the exterior periphery of at least the coronal superstructure connection portion. Such a tri-lobe structure may comprise three radially extending protrusions or indentations or grooves, each provided about 120° apart, running axially, either within the hollow axial channel of the coronal superstructure connection portion (for an internal tri-lobe) or along an exterior periphery of the omni-abutment (for an external tri-lobe). In another embodiment, the lobes may be unevenly distributed, with two such lobes being closer together than the third lobe (the lobe may be a protrusion or indentation/groove). In another embodiment more or less than 3 of such protrusions or indentations may be provided (e.g., providing something other than a tri-lobed structure such as exhibiting more than 3 such lobes, such as 4 lobes, 5 lobes, 6 lobes, or some other number). In a particular embodiment, the exterior periphery may not have a tri-lobe configuration, but may be generally ovoid in shape, but the hollow axial channel of the coronal superstructure connection portion may include a tri-lobe configuration, where the angle between such lobes may not be uniformly 120° (e.g., two of the lobes may be closer together than the $3^{rd}$ lobe).

In any of the described embodiments, the omni-abutment can include a central axial hollow portion or channel, e.g., wherein the hollow portion or channel may include a tri-lobe or other lobed configuration in a coronal top portion of the omni-abutment.

In any of the described embodiments, the omni-abutment can include one or more recessed portions or grooves (e.g., vertical grooves and/or horizontal grooves) or indentations in an exterior periphery of the coronal superstructure connection portion of the omni-abutment, for reception of a composite or other curable material for adhering the omni-abutment to an associated gingival healing cuff. Such structures may aid in retaining the gingival healing cuff in place.

In any of the described embodiments, the abutment can be formed of a material that is transparent to UV or other curing light wavelengths, such that UV or other curing light directed into the hollow axial channel of the omni-abutment passes through portions of the adjacent wall to assist in curing composite or other curable materials used to connect a gingival healing cuff or other device to the abutment.

In any of the described embodiments, even if the abutment is not formed of a material that is transparent to UV or other curing light wavelengths (e.g., such as titanium, zirconium, titania, zirconia, etc.), UV or other light curing of a given composite or other desired curable material used for bonding two structures together (e.g., the abutment and a cuff) may still be possible by providing perforations through such abutment, to allow transmission of UV or other curing light wavelengths therethrough.

Furthermore, Applicant has found, somewhat surprisingly, that it is possible to cure a composite used to adhere the two structures (the abutment and the gingival healing cuff) together simply by directing the curing light to the structures to be adhered, from an exterior of the assembly, without significant problems. Nevertheless, the above described features could be provided, where curing may otherwise be incomplete without such features.

In any of the described embodiments, the omni-abutment may include an abutment platform upon which the gingival healing cuff sits and mates with the platform (e.g., with any irregular features included within such platform).

In any of the described embodiments, a collar may be provided under the platform, between the apical connection portion and the platform. Such a collar may provide various features, including irregular surface features that are helpful in determining orientation when scanning, aiding with seating of a retention screw that engages in the implant, surface structure that allows for bone and/or soft tissue attachment, and/or verification of the seating of the abutment into the implant.

In any of the described embodiments, any included platform may include a platform marker (e.g., a protrusion or recess) that assists in verification of the correct seating of the gingival healing cuff on the platform. Such structure can also aid in scanning (providing an additional irregularity), and may provide additional retention to the gingival healing cuff.

In any of the described embodiments, vertical and/or horizontal grooves and/or round, circular or other shaped indentations may be provided in the coronal superstructure connection portion, to aid in retention of the gingival healing cuff, as well as provide additional irregularities for scanning, to better determine orientation.

In any of the described embodiments, generally axial or vertically extending indentations or recesses may be provided, e.g., running along the exterior peripheral surface of the collar, to assist in verification of the seating of the abutment into the implant and orientation of the abutment with the implant. Such structures also aid in scanning, and also assist in verification of proper seating of the gingival healing cuff.

In any of the described embodiments, vertical grooves may be provided in the hollow axial channel in the interior portion of the coronal superstructure connection portion (e.g., which may have a tri-lobe configuration). Such grooves assist in seating of items that may be helpful during scanning (e.g., receipt of a scanning body, or when taking an impression (e.g., an impression post or impression analog), or verification of implant stability (e.g., torque wrench, percussion insert for percussion testing of stability, or the like).

In any of the described embodiments, the inner surface of the coronal superstructure connection portion may be internally threaded to allow for increased secure seating of any such items (e.g., scanning bodies, impression posts or analogs, torque wrenches, percussion inserts, or the like). Another possible mechanism for securing of such an item would be a configuration in which the insert (e.g., scanning bodies, impression posts or analogs, torque wrenches, percussion inserts, or the like) may be secured into the threading or other connection of the dental implant itself. For example, one could remove the retaining screw that couples the abutment into the implant, and insert the desired insert into the top of the abutment, where such insert could include threading or other coupling mechanism, that allows the insert to couple directly into the dental implant itself (the dental implant underlying the abutment).

In any of the described embodiments, retention grooves could be provided in the interior tri-lobe or similar grooved configuration to assist in secure seating and verification of the seating of mating portions of a coronal scanning body or other item inserted into such tri-lobe receptacle. A détente mechanism may be provided where the inserting structure includes a mating protrusion, which is retained within such retention groove. Means may be provided for releasing such a détente mechanism, allowing removal of the inserted structure, once it is no longer needed.

In any of the described embodiments, the apical connection portion may include at least one of a hex connection, a Narrow CrossFit (NC) connection, or any other connection at the apical connection portion.

The omni-abutment can be adjusted by a practitioner as to its height or other aspect of its shape, for example, the abutment can be adjusted vertically and/or horizontally. For example, a practitioner may choose to cut off or otherwise shorten the abutment, e.g., by removing a portion of the top coronal portion of the abutment. By way of example, the abutment may typically have a height ranging from about 3 mm to about 11 mm. A typical height may be from 8 mm to 11 mm. Exemplary heights may include 3 mm, 4 mm, 5 mm, 6 mm, 7 mm, 8 mm, 9 mm, 10 mm, or 11 mm.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures.

DETAILED DESCRIPTION OF THE PREFERRED EMBODIMENTS

I. Definitions

Figure 1A:
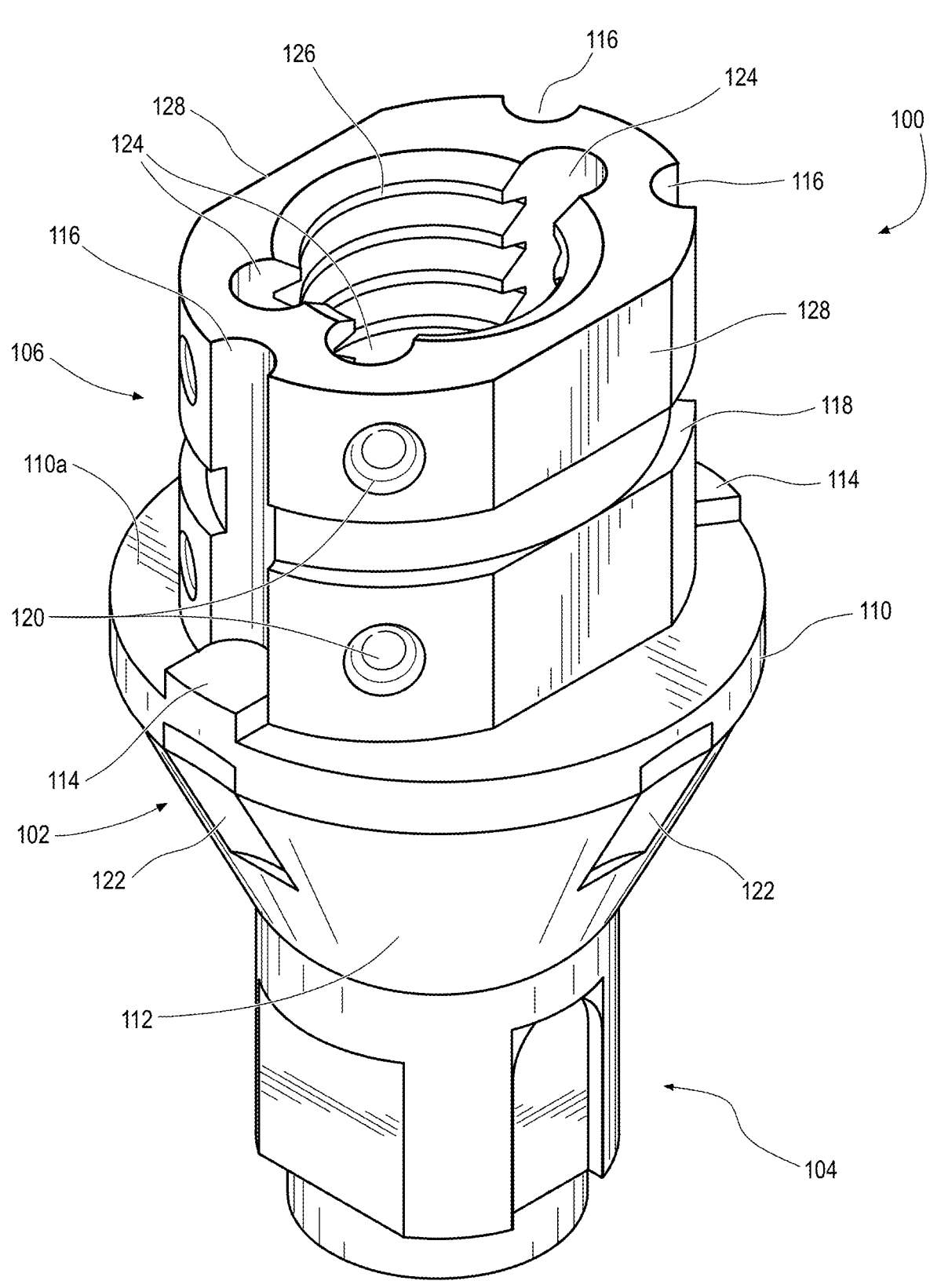
FIGS. 1A-1B illustrate a perspective and buccal front view of an exemplary omni-abutment according to an embodiment of the present disclosure.

Some ranges may be disclosed herein. Additional ranges may be defined between any values disclosed herein as being exemplary of a particular parameter. All such ranges are contemplated and within the scope of the present disclosure.

Numbers, percentages, ratios, or other values stated herein may include that value, and also other values that are about or approximately the stated value, as would be appreciated by one of ordinary skill in the art. A stated value should therefore be interpreted broadly enough to encompass values that are at least close enough to the stated value to perform a desired function or achieve a desired result, and/or values that round to the stated value. The stated values for example thus include values that are within 20%, 10%, within 5%, within 1%, etc. of a stated value.

All numbers used in the specification and claims are to be understood as being modified in all instances by the term "about", unless otherwise indicated. The use of "about", "substantially" and the like may particularly include values within the above stated variance (e.g., within 20%, 10%, 5%, 1%). Notwithstanding that the numerical ranges and parameters setting forth the broad scope of the subject matter presented herein are approximations, the numerical values set forth in the specific examples are reported as precisely as possible. Any numerical value, however, inherently contains certain errors necessarily resulting from the standard deviation found in their respective testing measurements.

It must be noted that, as used in this specification and the appended claims, the singular forms "a," "an" and "the" include plural referents unless the content clearly dictates otherwise.

Any directions or reference frames in the description are merely relative directions (or movements). For example, any references to "top", "bottom", "up" "down", "above", "below" or the like are merely descriptive of the relative position or movement of the related elements as shown, and it will be understood that these may change as the structure is rotated, moved, the perspective changes, etc.

All publications, patents and patent applications cited herein, whether supra or infra, are hereby incorporated by reference in their entirety to the same extent as if each individual publication, patent or patent application was specifically and individually indicated to be incorporated by reference.

II. Introduction

In one embodiment, the present invention is directed to an omni-abutment that includes (i) an apical connection portion that would mate/attach with the receiving portion on a corresponding implant; and (ii) a coronal superstructure connection portion that serves as a core for attachment of a gingival healing cuff and/or a final crown prosthesis, where the coronal superstructure connection portion is connected to the apical connection portion either as one homogenous single piece of material or provided as different biocompatible materials. While in an embodiment, the omni-abutment may be separate from the gingival healing cuff, in another embodiment, it will be appreciated that both structures could be formed as a single piece of seamless material (e.g., 3D printed from a resin material, machined, or otherwise manufactured). In an embodiment, at least the coronal superstructure connection portion of the omni-abutment may include an irregular ovoid transverse cross-section, and/or a tri-lobe interior and/or exterior structure, wherein a selected exterior configuration of the coronal superstructure is not fully symmetrical (e.g., not a simple cylinder, oval, or similar highly symmetrical structure, as it is difficult to determine orientation and position when scanning such structures). The present abutment is configured with a variety of irregularities in any otherwise generally uniform shape so as to allow digital scanning of such structure in a way that allows the practitioner to determine orientation relatively easily and with certainty.

A gingival healing cuff can also be provided. The cuff fits over the omni-abutment, wherein the gingival healing cuff may include a corresponding keyed configuration for receipt of the irregular ovoid, tri-lobe or other specific structure provided by the exterior periphery of the coronal superstructure connection portion of the omni-abutment. The various structures provided in the omni-abutment as shown in the Figures and described herein provide functionality not available in current systems. The term omni-abutment is used, as the present configurations provide far more functionality than provided within current abutments.

III. Exemplary Methods and Systems

Figure 1B:
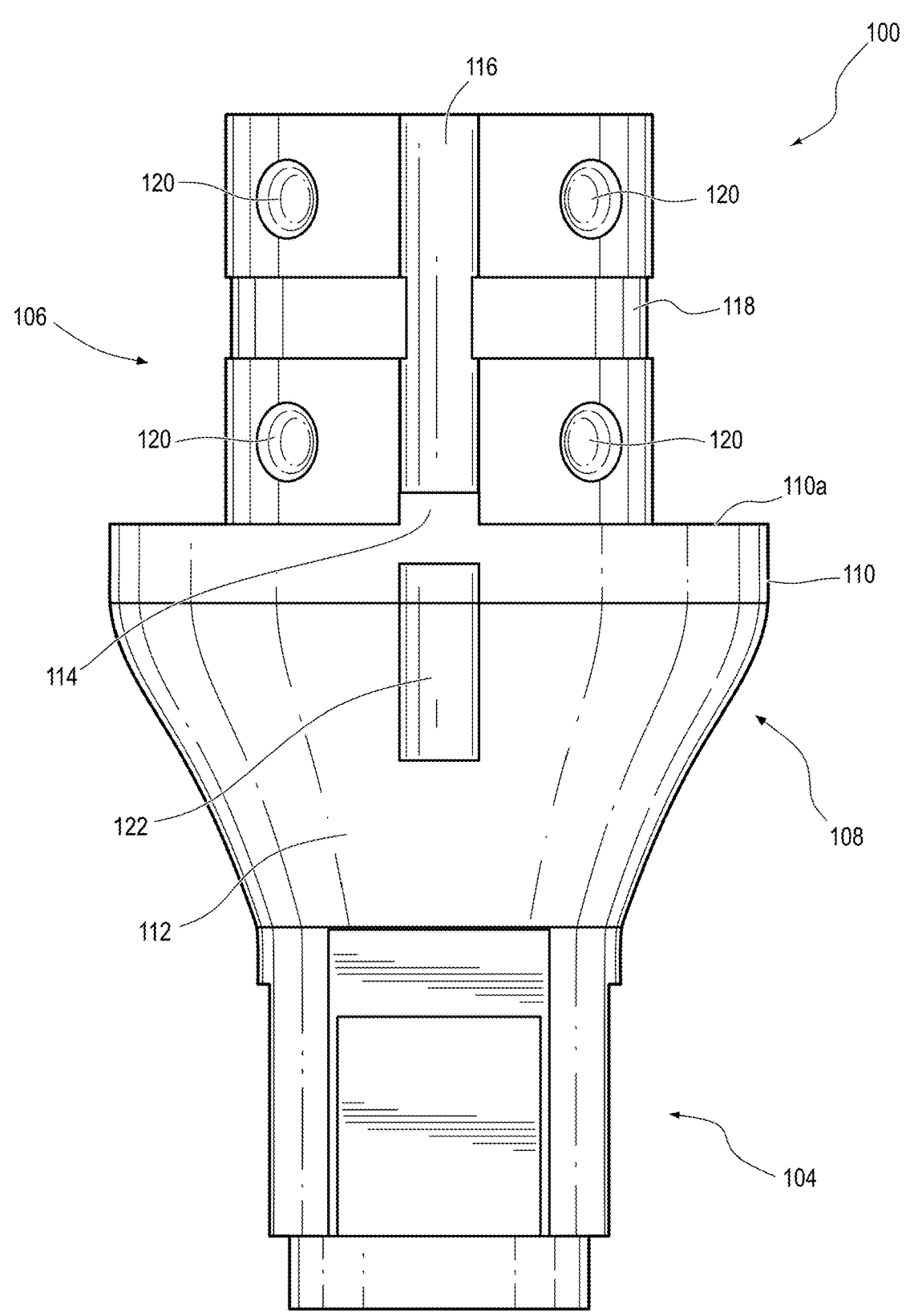

FIGS. 1A-1B illustrate an exemplary omni-abutment 100 provided as a single piece body 102, including an apical connection portion 104 and a coronal superstructure connection portion 106. As shown in FIG. 1B, an abutment superstructure 108 may include both coronal superstructure connection portion 106, as well as an abutment platform 110, and a collar 112. Apical connection portion 104 includes an indexed engaging connection that mates with a corresponding connection in a dental implant. The indexed engaging connection can be configured for any desired dental implant (e.g., any of the wide variety of commercially available dental implants, or otherwise). The connection at the apical connection portion 104 may be engaging (e.g., indexed keyed structure) or a non-engaging connection (which allows rotation). A non-engaging connection is round in cross-sectional shape, without any indexing. Implant abutments come in two types, engaging and non-engaging.

Engaging can be used in any situation for restorative purposes. A non-engaging connection may be used when two or more implants are tied together with a prosthesis, e.g., bridge, denture, metal or zirconium structure. When they are tied together, they will not rotate, hence no indexing is necessary. The abutment superstructure 108 allows establishment of the gingival emergence profile, which ultimately shapes the gingival tissue from the implant connection to the crest of the gingival tissue. This superstructure 108 also includes many other advantageous substructures, as described herein, that allow for many additional functions.

Such functions may include the below features, as well as additional features described herein. For example, the features of the omni-abutment superstructure, alone or mated with a gingival healing cuff or other attachment, allow for determination of rotational "timing" and orientation of the abutment with the dental implant and surrounding oral tissues (hard/and or soft) for ultimate fabrication of a provisional or final dental prosthesis. This can either be done via scanning, direct visualization, x-ray, etc.

Another feature is that the coronal superstructure connection portion of the omni-abutment may extend to (e.g., flush with) or coronally out of the attached gingival healing cuff. The most superior surface of the superstructure connection portion may have identifying landmarks such as grooves and/or other markers that can be scanned or used with an analog impression to allow for determination of orientation of the abutment and/or associated gingival healing cuff with the surrounding oral anatomic structures for ultimate fabrication of a dental prosthesis. This is superficially similar to techniques being used by some practitioners, but significantly different in that it uses the omni-abutment as the scan body (no separate scanning body is required) and may include the gingival healing cuff. To Applicant's knowledge, no one else is using a "core" abutment for either scanning or analog impression purposes. Such features are described in items 12 and 13 of the Appendix of Provisional Application Ser. No. 63/557,379, filed Feb. 23, 2024, and titled "OMNI-ABUTMENT CORE AND METHODS OF USE, herein incorporated by reference in its entirety.

As another feature, ideally, the omni-abutment can be used as a provisional abutment with a gingival healing cuff. Also, it can be used as a final abutment for a final prosthesis. The exact same abutment can be used for both purposes, sequentially.

As another feature, the omni-abutment and gingival healing cuff or provisional/final prosthesis can be manufactured out of one homogenous seamless material, or as a combination of biocompatible materials.

As another feature, the apical connection portion may have a configuration that allows it to be scanned in a way that the practitioner can determine orientation with certainty, separate from or in addition to any structures that may provide similar functionality in the more coronal portions of the omni-abutment and/or gingival healing cuff, for determining orientation of the omni-abutment relative to surrounding oral anatomical structure and the implant, for fabrication of a prosthesis. The present omni-abutments and/or gingival healing cuffs may be used with a coronal and/or apical scanning body.

The abutment platform 110 includes a coronal top surface 110a on which the gingival healing cuff sits, and mates with platform 110. Platform also is shown as including additional features that assist in scanning (e.g., digital scanning, CT scanning, ultrasound, photogrammetry, or other image scanning) of the abutment 100 and a connected prosthesis.

Coronal superstructure connection portion 106 is a connection portion of the overall superstructure 108, which is important to several functions. For example, it provides a surface for retention and alignment of anatomic and/or non-anatomic healing cuffs, e.g., varieties of which are described in Patent Application Ser. No. 63/710,443, filed Oct. 22, 2024, titled "3D PRINTED OR OTHER ANATOMICAL AND CIRCULAR GINGIVAL CUFFS, herein incorporated by reference in its entirety. Of course other gingival healing cuffs may also be used.

Coronal superstructure connection portion 106 also provides surface features that are helpful in scanning (particularly in determining orientation and position), as well as seating of devices to test the stability of the underlying dental implant, and seating of devices used to take an analog impression, or to seat a scanning body. Such can also include seating of devices upon which a prosthesis can be seated. Such a concept would bridge the gap between use of an engaging omni-abutment for single restorations, to allowing one to use non-engaging omni-abutments for bridges and dentures. Such a use may very well require a change in the configuration of the outer surface of the coronal superstructure connection portion of the omni-abutment, but the internal connection portion may very well remain the same.

Collar 112 is positioned between platform 110 and apical connection portion 104. The illustrated collar 112 is frusto-conical in shape (i.e., a truncated cone, also known as a frustum). While a particular shape is shown, it will be appreciated that this collar and/or platform 110 may be anatomical or non-anatomical in shape. An anatomical shape may also be generally frustoconical in shape, with a similar generally conical taper, although with some variations in shape, to better approximate the actual anatomy where inserted and received. In addition, these structures can possess features that assist in scanning, seating of the retention screw that engages in the implant (attaching the abutment to the implant), and other features. For example, collar 112 may provide surface structure (e.g., texturing, or simply choice of materials) that facilitates bone and or soft tissue attachment thereto. The collar 112 may also aid in verification of the seating (full seating) of the abutment into the implant.

As shown, platform 110 may include one or more platform markers 114 that are useful in assisting in verification of the correct seating of the gingival healing cuff on platform 110. The presence of such markers (shown as an upwardly extending protrusion in FIG. 1A) also aid in scanning of the abutment and an attached gingival healing cuff. As shown, one important feature of the illustrated protruding platform marker 114 is that an edge of such marker 114 is flush with the radial edge of platform 110, so that even when a gingival healing cuff is seated on platform 110, marker 114 will be visible, both by eye, and through scanning, even if gingival healing cuff is not radiographically transparent to whatever imaging system is employed in such scanning. This allows a practitioner to verify that the gingival healing cuff is in fact properly seated on platform 110, without any undesirable gap therebetween. Such a marker 114 may also aid in retaining the gingival healing cuff over the abutment 100, to prevent undesirable detachment, or rotation.

Coronal superstructure connection portion 106 is also shown as including one or more (e.g., 3 are illustrated) substantially vertical grooves or other recessed portions 116 in an exterior peripheral surface of the abutment. Such features aid in alignment and retention of the gingival healing cuff, as well as providing surfaces that detract from the regularity of the otherwise ovoid cross-sectional shape of the coronal connection portion 106, aiding in scanning of the abutment. Such grooves or other recessed portions may also serve for reception of a composite or other curable material for adhering the abutment to an associated gingival healing cuff. While recessed portions 116 are shown as substantially vertical, running axially, it will be appreciated that they could be provided at another angle, e.g., between vertical and horizontal (e.g., they could run at a diagonal angle such as within 45°, within 30° or within 10° of vertical, should such be desired). In addition, while 3 such grooves or recessed portions are shown, it will be appreciated that more or fewer could be provided.

In an embodiment, the illustrated unequal placement of the grooves or recessed portions 116 is advantageous, as the single groove located by itself may serve as an alignment marker, denoting the buccal face, while the two grooves or recessed portions 116 shown opposite the buccal groove or recess may denote the lingual face. It will be appreciated that other configurations are of course also possible.

Coronal superstructure connection portion 106 may also include one or more generally horizontal grooves or recessed portions 118, as shown. Such a horizontal groove or recessed portion provides similar functionality, aiding with retention of the gingival healing cuff to the abutment, as well as aiding with scanning of the abutment, as it also provides additional irregularity to the exterior surface. As with recessed portions 116, horizontal groove or other recessed portions 118 may serve for reception of a composite or other curable material for adhering the abutment to an associated gingival healing cuff. While recessed portion 118 is shown as substantially horizontal, running longitudinally around the exterior periphery of the coronal superstructure portion 106, it will be appreciated that it could be provided at another angle, e.g., between horizontal and vertical (e.g., it could run at a diagonal angle such as within 45°, within 30° or within 10° of horizontal, should such be desired). In addition, while a single such groove or recessed portion is shown, it will be appreciated that more such horizontal grooves could be provided.

FIGS. 1A-1B further illustrate the presence of one or more indentations 120 in the coronal superstructure portion 106 of abutment 100. Such indentations 120 may be rounded or circular in shape, as shown, or may be of another shape (e.g., square, rectangular, or other polygonal shaped). Any shape may be possible. Such indentations provide for improved retention of the gingival healing cuff as well as providing additional irregularities to the otherwise smooth exterior surface, which is helpful in determining orientation and position when scanning the abutment.

FIGS. 1A-1B also show the presence of a groove or recess 122 within the exterior surface of platform 110 and/or collar 112. It will be appreciated that such a structure could also or alternatively be a protrusion, or a combination of grooves and/or recesses with protrusions of various shapes and configurations. Any of such could be used to assist in verification of various steps as described herein. For example, such structures assist in verification of the seating of the abutment into the implant, and orientation of the abutment with the implant. Such features also aid with scanning of the abutment (as they provide another irregularity to the otherwise smooth exterior surface). Such structures 122 also serve to assist in verification of the proper seating of the gingival healing cuff. The illustrated abutment includes 4 such recesses 122, although more or fewer could be provided. The illustrated recesses 122 are evenly distributed about the abutment (e.g., 90° apart from one another).

It will also be noted that in the illustrated embodiment, two of the recesses 122 are axially aligned with protruding platform markers 114.

As shown in FIG. 1A, abutment 100 may include indentations 124 in the interior hollow axial channel of the coronal superstructure connection portion 106 of abutment 100. Such interior indentations or grooves allow for seating of various items that assist with scanning, impression taking, and verification of implant stability (e.g., insertion of a scanning body, impression post, impression post analog, torque wrench, percussion torque testing instrument, or other torque test instrument). Such features may also be used for verifying proper seating of a device upon which a temporary or final prosthesis can be seated. The illustrated interior indentations may be considered to provide a tri-lobe interior structure configuration. As shown, in an embodiment, 3 lobes or indentations may be provided, unevenly distributed about the hollow axial channel of coronal superstructure portion 106. For example, one such lobe may be positioned centered between the two exterior peripheral vertical grooves or recessed portions 116 (on the lingual face), while the other exterior peripheral vertical groove or recessed portion 116 (on the buccal face) may be centered between the other two lobes 124, as shown.

Figures 4A, 4B:
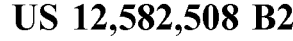
FIGS. 4A-4B illustrate a perspective view and a cross-sectional view of an omni-abutment similar to that of FIGS. 1A-1B, but including a retention groove 125 as an undercut within the vertical interior indentations 124, for additional retention or locking of a structure inserted into such indentations.

As shown, the substantially vertical indentations 124 may extend downward, within the hollow axial channel of coronal superstructure connection portion 106, e.g., to a depth that terminates at or before the top surface 110a of platform 110. The indentations may be arranged to provide a keyed configuration, to ensure that any structure inserted into the top end of the hollow axial channel of coronal superstructure portion 106 can only be inserted in a single orientation, and cannot rotate (i.e., is locked) once inserted. Each vertical indentation 124 could further include a retention groove or similar structure 125 (sec FIGS. 4A-4B), to assist in secure seating and verification of the seating of the mating portions of a coronal scanning body or other item that may be placed into such grooves, channels, or the like. For example, a small indentation 125 may be present in a middle portion or another location within indentation 124, for such purpose. By way of example, a détente or other mating protrusion in the structure being seated may mate into, and be retained by such small indentation 125.

FIG. 1A also illustrates how the hollow axial channel of coronal superstructure portion 106 may be threaded, e.g., including threads 126 in such inner surface, allowing for increased secure seating of any items coupled or inserted into the top end of the hollow axial channel of the coronal superstructure portion 106. Such threading may extend only partially through the full height of the abutment, e.g., no further than the top surface 110a or platform 110. The hollow axial channel itself may extend through the entire length of the abutment, e.g., allowing insertion of a retention screw used to attach the apical connection portion 104 into a corresponding underlying dental implant. Another possible mechanism for securing an insertable insert tool (e.g., scanning bodies, impression posts or analogs, torque wrenches, percussion inserts, or the like) may employ the coupling mechanism within the underlying dental implant. For example, one could remove the retaining screw that couples the abutment into the implant, and insert the desired insert into the top of the abutment, where such insert could include threading or other coupling mechanism, that allows the insert to couple directly into the dental implant itself (the dental implant underlying the abutment).

The illustrated generally ovoid transverse cross-section of the coronal superstructure connection portion 106 is shown as including flattened surfaces 128 on such connection portion 106, which flattened faces allow for orientation and retention of the gingival healing cuff, as well as provide for improved scanning. Such flattened surfaces are shown positioned at the mesial and distal faces of the coronal superstructure connection portion of the abutment. Such flattening (reducing mesial-distal width) is also helpful in accommodating use of the same abutment in all tooth positions, including the smallest of the lower incisor tooth positions (which are the smallest teeth in a given patient).

Figure 2:
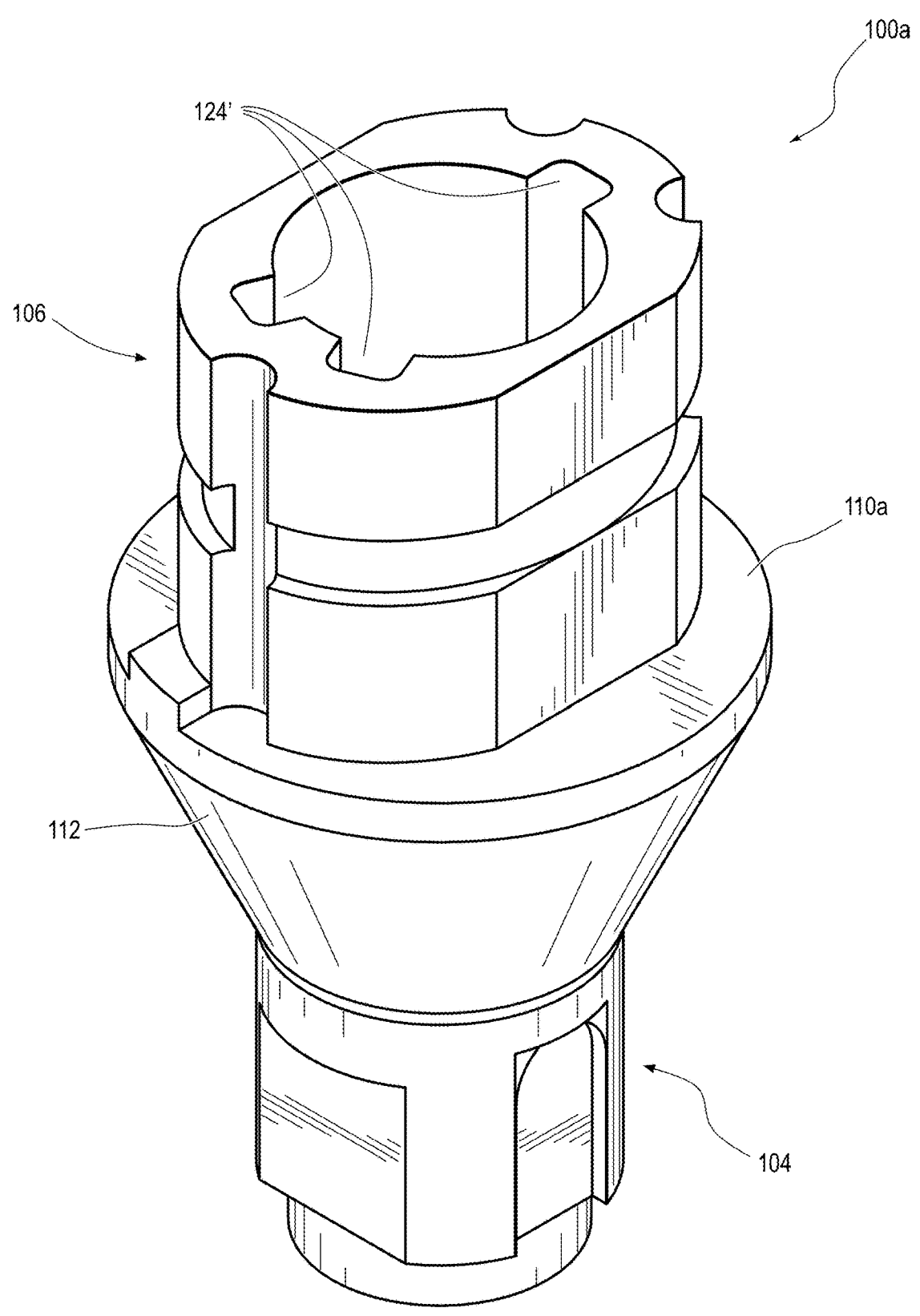
FIG. 2 illustrates a perspective view of another exemplary omni-abutment according to another embodiment of the present disclosure.

FIG. 2 illustrates another exemplary abutment 100*a*, e.g., including similar features to those described for abutment 100 in FIGS. 1A-1B. Some principal differences include the lack of various optional features (e.g., internal threading 126 within abutment 100*a*, indentations 120, recesses 122), as well as a more square shape to the interior indentations 124' in the hollow axial channel of coronal superstructure connection portion 106.

Figure 3:
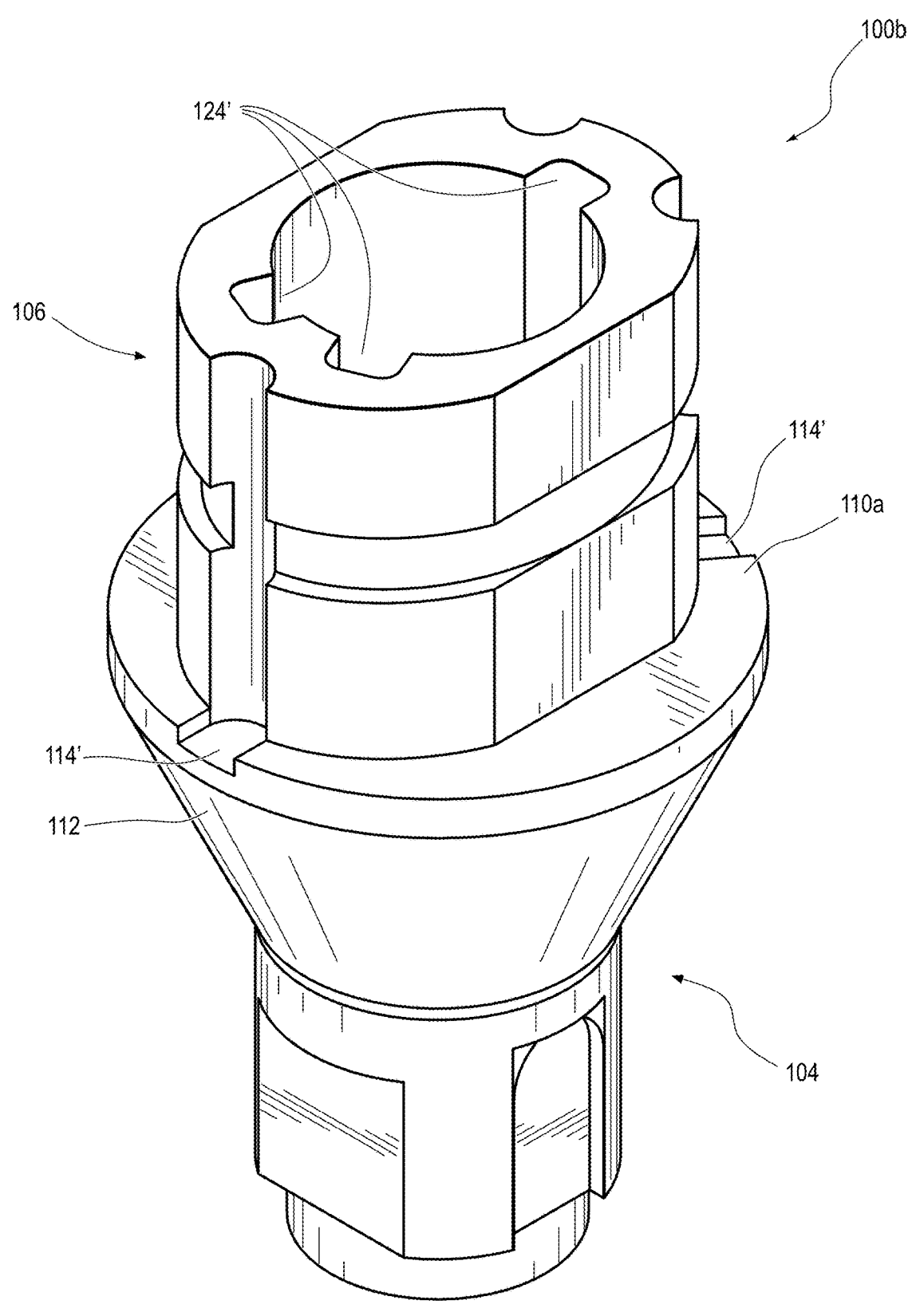
FIG. 3 illustrates a perspective view of another exemplary omni-abutment according to another embodiment of the present disclosure.

FIG. 3 illustrates another exemplary abutment 100*b*, e.g., including similar features to those described for abutments 100 and 100*a* in FIGS. 1A-2. A principal difference includes the inclusion of a differently configured platform marker 114', which is not configured as a protrusion extending from top platform surface 110*a*, but is configured as a depression or recess, within the top platform surface 110*a*, as shown.

Figure 5:
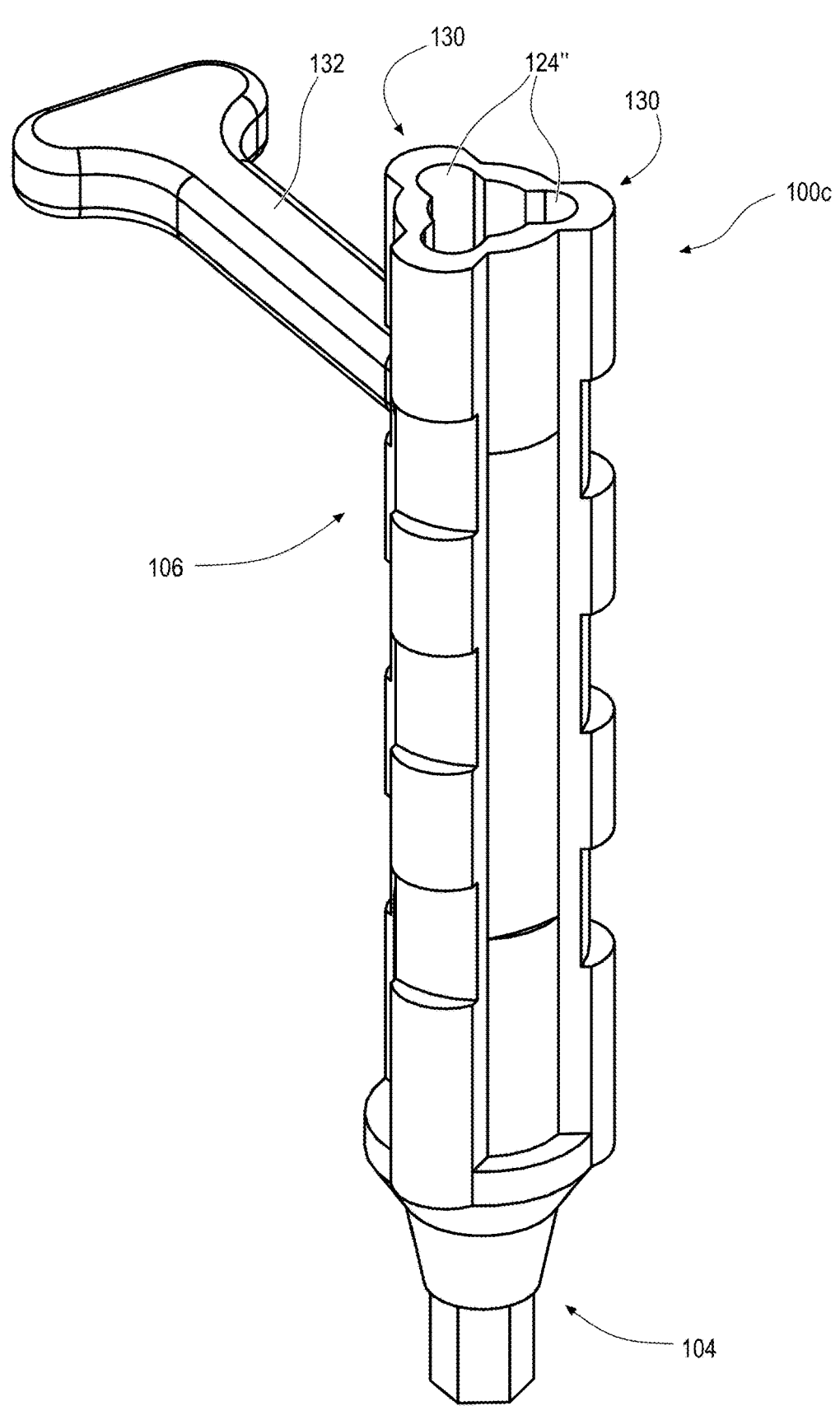
FIG. 5 illustrates a perspective view of another exemplary omni-abutment according to another embodiment of the present disclosure.
Figure 6A:
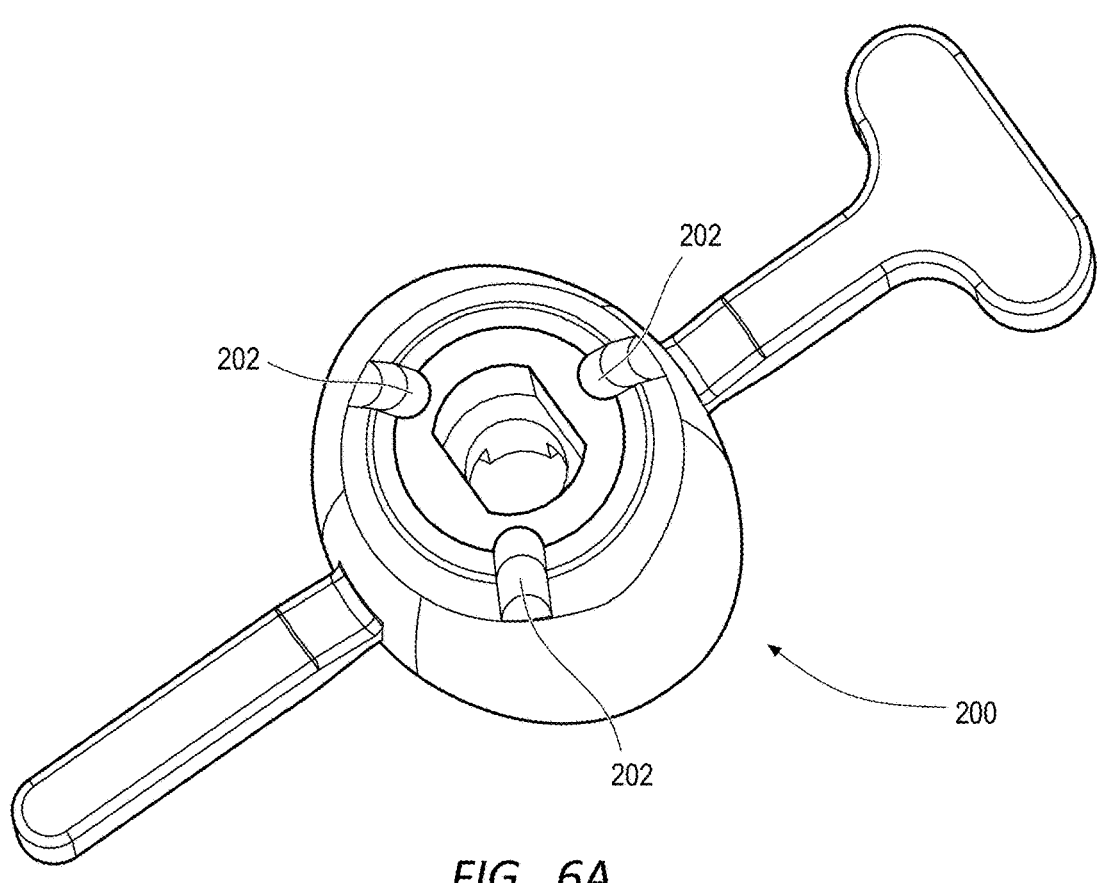
FIGS. 6A-6B illustrate bottom and top perspective views of an exemplary gingival healing cuff that may be used with an omni-abutment according to an embodiment of the present disclosure.
Figure 6B:
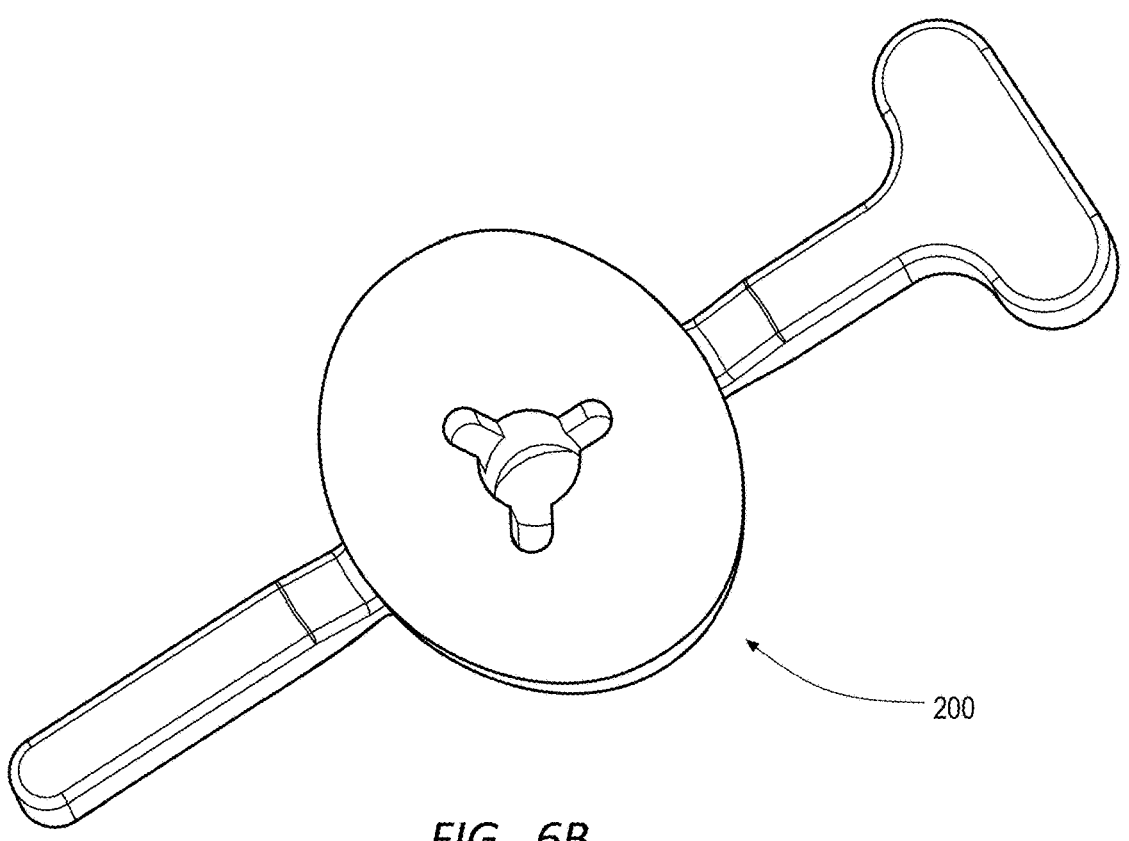
Figure 7A:
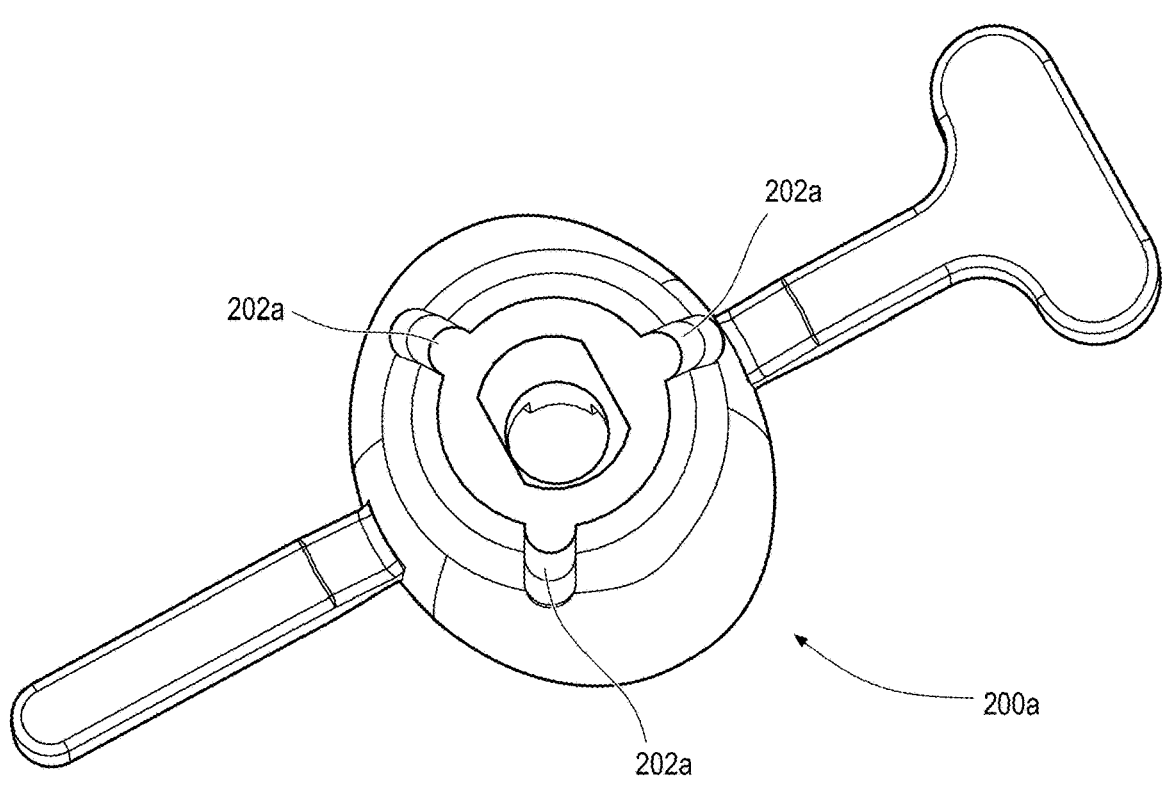
FIGS. 7A-7B illustrate bottom and top perspective views of another exemplary gingival healing cuff that may be used with an omni-abutment according to an embodiment of the present disclosure.
Figure 7B:
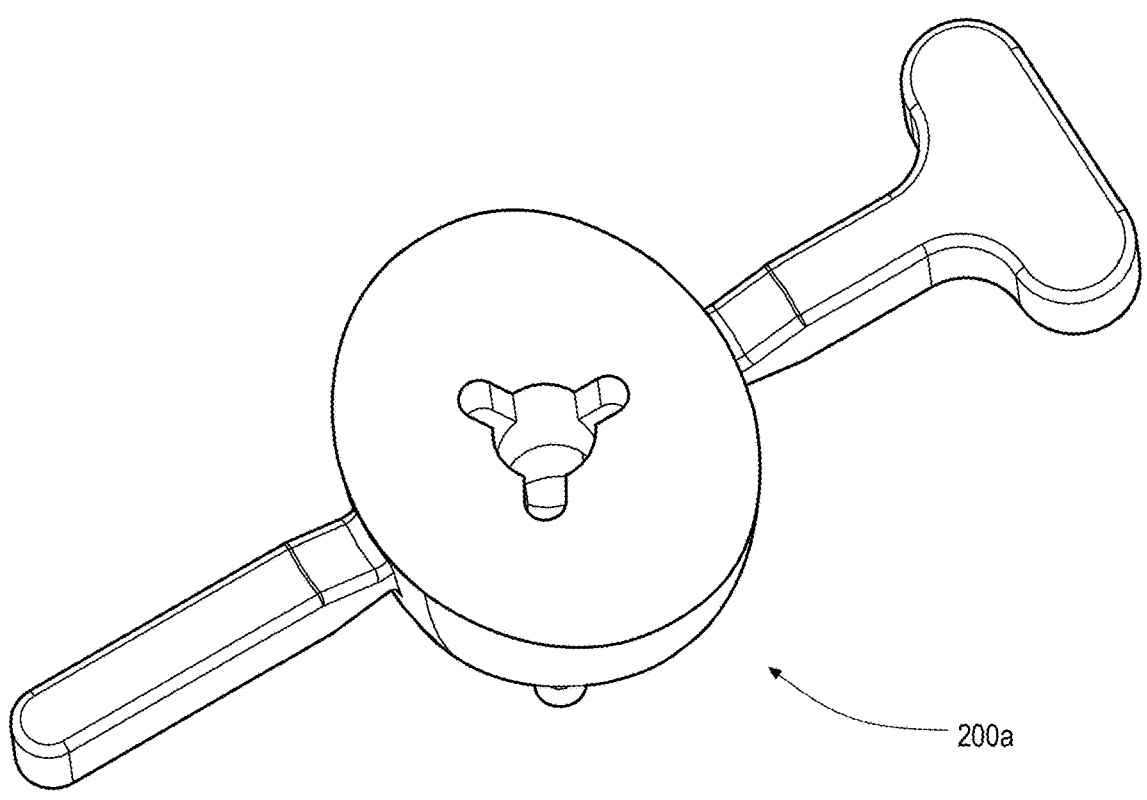
Figure 8A:
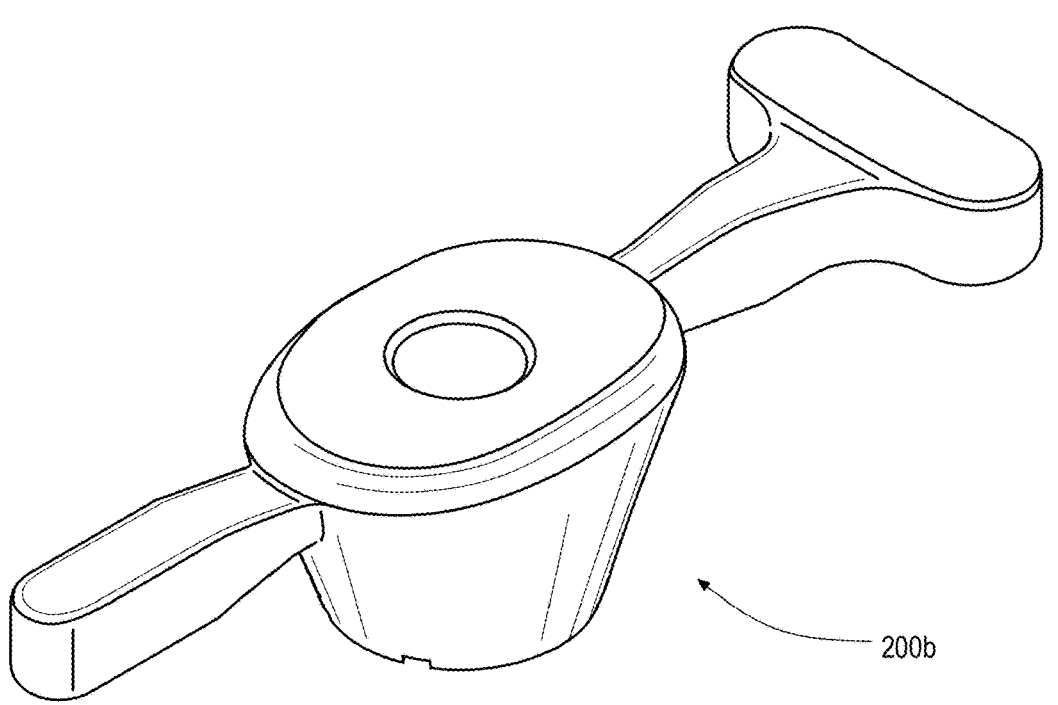
FIGS. 8A-8B illustrate bottom and top perspective views of another exemplary gingival healing cuff that may is specifically configured for use with the omni-abutment of FIGS. 1A-1B, or 4A-4B.
Figure 8B:
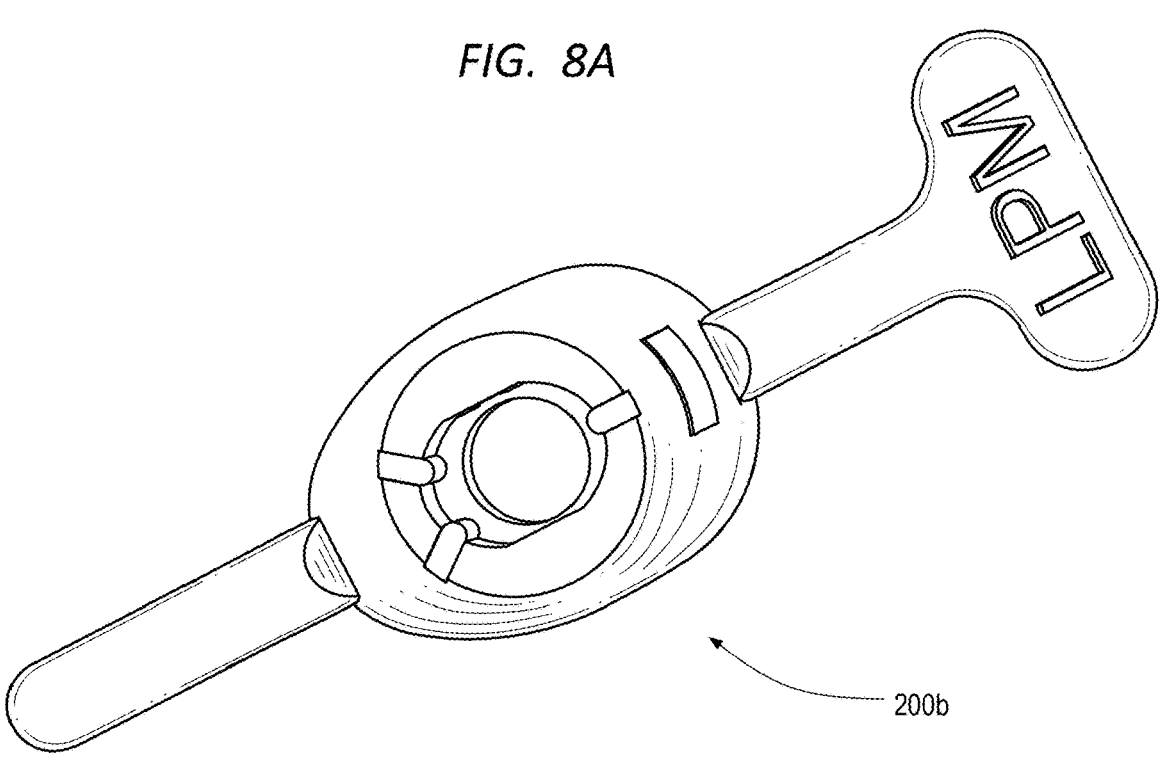
Figures 8C, 8D:
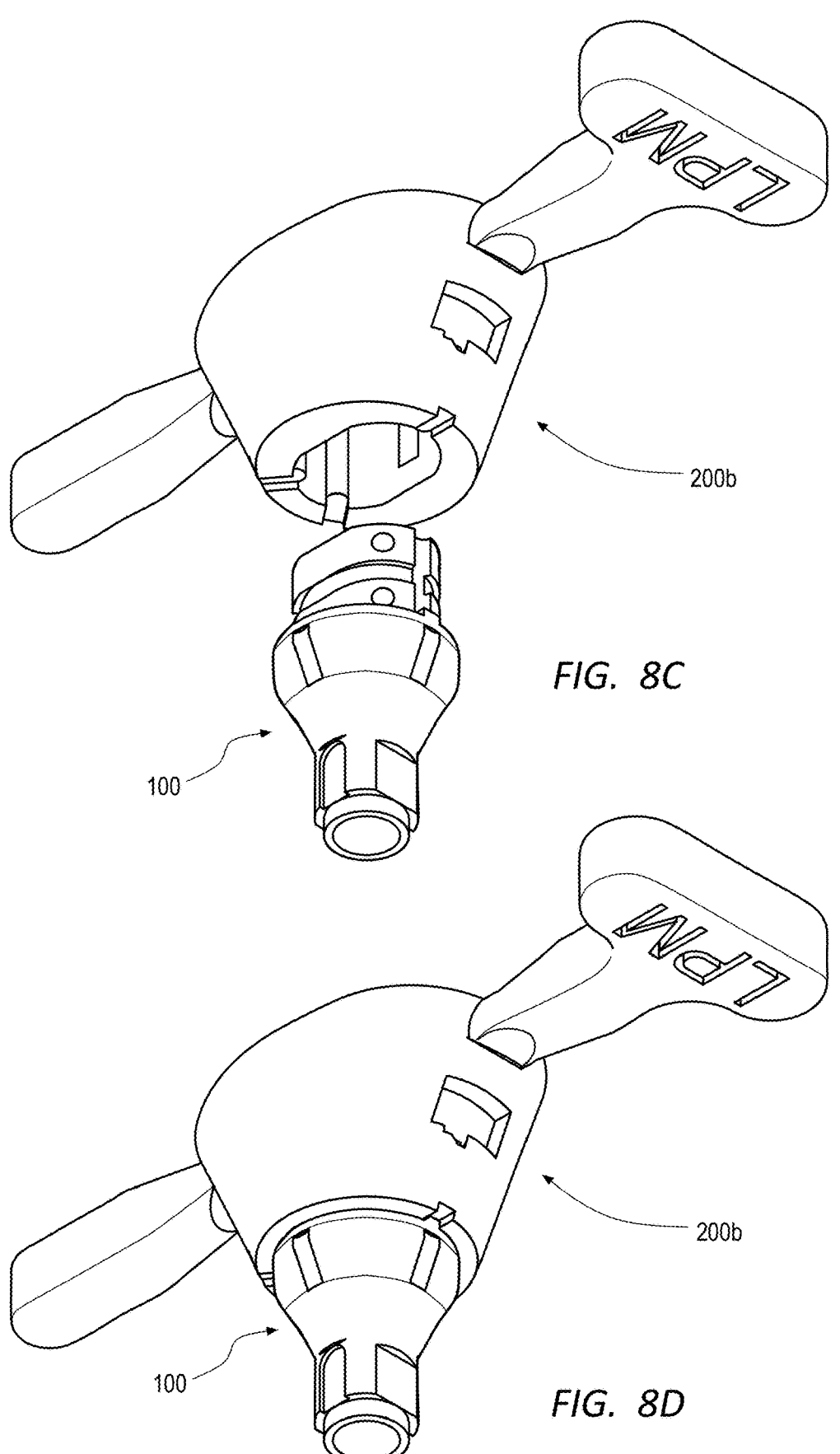
FIGS. 8C-8D illustrate the gingival healing cuff of FIGS. 8A-8B mated with the omni-abutment of FIG. 1A-1B or 4A-4B.

FIG. 5 illustrates another exemplary abutment 100*c*, which similarly includes an apical connection portion 104 and a coronal superstructure connection portion 106. Abutment 100*c* is shown as including a tri-lobe configuration both at the interior (with respect to tri-lobe vertical indentations 124', as well as a tri-lobe configuration at the exterior periphery surface designated at 130. Such a tri-lobe configuration provides for good scanning ability, and the ability to recognize orientation and position when taking a scan using such an abutment. A T-shaped handle 132 is also shown attached at a buccal face. Such a handle may be removable. The apical connection portion shows use of a hex connection, while the apical connection portions of abutments 100, 100*a* and 100*b* illustrate a different apical connection configuration. It will be appreciated that any apical connection configuration may be provided.

Any of the described omni-abutments may be formed from any desired biocompatible material (e.g., titanium, biocompatible ceramics, 3D printed from a biocompatible resin, or the like). The omni-abutment may be precision milled, injection molded, or may be 3D printed (e.g., 3D printed metal, or 3D printed polymer resin). The gingival healing cuffs may be similarly formed (e.g., 3D printed, injection molded, or milled). Other manufacturing methods and materials may also be possible when fabricating any of the components. In an embodiment, the gingival healing cuffs are formed from a non-metallic material, allowing them to be easily shaped chair-side, should the practitioner so choose.

FIGS. 6A-6B and 7A-7B illustrate exemplary gingival healing cuffs that may be used with a corresponding abutment. For example, gingival healing cuffs 200 and 200*a* of FIGS. 6A-6B may couple over the coronal superstructure connection portion of a complementary shaped abutment. The principal difference between illustrated gingival healing cuffs 200 and 200*a* is the presence of the mating recesses 202 at the bottom of cuff 200, while cuff 200*a* is shown as including mating protrusions. FIGS. 8A-8D illustrate another exemplary gingival healing cuff 200*b* that is specifically configured for use with the omni-abutments of FIGS. 1A-1B, and FIGS. 4A-4B.

Gingival healing cuffs including features such as those shown and described in Applicant's Patent Application Ser. No. 63/710,443, filed Oct. 22, 2024, titled "3D PRINTED OR OTHER ANATOMICAL AND CIRCULAR GINGIVAL CUFFS, herein incorporated by reference in its entirety, may be suitable for use. A wide variety of other gingival healing cuffs may also be used with the present omni-abutment.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

The invention claimed is:

1. An omni-abutment comprising:
   (i) an apical connection portion that is configured to mate and/or attach with the receiving portion on a corresponding implant;
   (ii) a coronal superstructure connection portion serving as a core that is connected to the apical connection portion either as one homogenous single piece of material or as different biocompatible materials, and wherein at least the coronal superstructure connection portion of the omni-abutment includes a tri-lobe interior structure and a tri-lobe exterior structure, wherein the omni-abutment includes a platform and a collar between the apical connection portion and the coronal superstructure connection portion, the collar including a frustoconical shape with a frustum of the frustoconical shape tapering from a top surface of the platform towards the apical connection portion; and wherein the platform comprising a protruding platform marker that is flushed with a radial edge of the platform.

2. The omni-abutment as recited in claim 1, wherein an exterior configuration of the coronal superstructure is not fully symmetrical and includes one or more irregularities, so as to allow digital or analog scanning of such structure in a way that allows the practitioner to determine orientation of the omni-abutment with certainty relative to surrounding oral tissues and the corresponding implant.

3. The omni-abutment as recited in claim 2, wherein such scanning includes at least one of CT scanning, x-ray, ultrasound, photogrammetry or other scanning technology.

4. The omni-abutment as recited in claim 1, wherein an exterior configuration of the coronal superstructure is not fully symmetrical and includes one or more irregularities, so as to allow a dental impression of such to be used in a way that allows the practitioner to determine orientation of the omni-abutment with certainty relative to surrounding oral tissues and the corresponding implant.

5. The omni-abutment as recited in claim 2, further comprising:
   an irregular ovoid transverse cross-section provided along the exterior periphery of the coronal superstructure connection portion of the omni-abutment.

6. The omni-abutment as recited in claim 5, wherein the irregular ovoid including relatively shorter buccal and lingual faces, and relatively longer mesial and distal faces, wherein the mesial and distal faces include a truncated flattened surface to accommodate use of the omni-abutment in all tooth positions, including the smallest of lower incisor tooth positions.

7. The omni-abutment as recited in claim 5, wherein the omni-abutment includes a platform and a collar between the apical connection portion and the coronal superstructure connection portion, the platform and/or collar being anatomically shaped.

8. The omni-abutment as recited in claim 5, further comprising one or more alignment indents or one or more alignment protrusions in a coronal top surface of the platform.

9. The omni-abutment as recited in claim 5, wherein the omni-abutment includes a central axial hollow portion or channel, wherein the hollow portion or channel also includes tri-lobe grooves as part of the tri-lobe interior structure within a coronal superstructure connection portion of the omni-abutment, for mating with a correspondingly shaped scanning body, torque wrench, percussion insert or other insert.

10. The omni-abutment as recited in claim 5, wherein the coronal superstructure connection portion of the omni-abutment includes one or more recessed portions in an exterior periphery of the omni-abutment, for reception of a composite or other curable material for adhering the omni-abutment to an associated gingival healing cuff.

11. The omni-abutment as recited in claim 10, wherein the recessed portions run both axially and longitudinally around the exterior periphery of the coronal superstructure connection portion of the omni-abutment.

12. The omni-abutment as recited in claim 5, wherein the apical connection portion comprises at least one of a hex connection or any other connection at the apical connection portion.

13. The omni-abutment as recited in claim 5, further comprising internal threads within a central axial hollow portion or channel of the omni-abutment, for threaded attachment of a scanning body, impression post, torque wrench, percussion insert, or other insert.

14. The omni-abutment as recited in claim 5, wherein the apical connection portion includes an engaging configuration that allows it to be scanned in a way that the practitioner can determine orientation of the abutment with certainty, relative to surrounding oral anatomical structure and the corresponding implant, use of such in fabrication of a prosthesis.

15. The omni-abutment as recited in claim 5, wherein the omni-abutment is adapted to be used to support a provisional or final prosthesis.

16. The omni-abutment as recited in claim 5, wherein the omni-abutment is adapted to be adjusted by a practitioner as to its height by shortening the abutment.

17. The omni-abutment as recited in claim 5, wherein the omni-abutment is adapted to be horizontally adjusted by a practitioner.

18. An omni-abutment and gingival healing cuff system, comprising the omni-abutment as recited in claim 2, and a gingival healing cuff that fits over the omni-abutment, wherein the gingival healing cuff includes a corresponding structure for receipt of the tri-lobe exterior structure of the omni-abutment, so as to mate the two together in a keyed arrangement.

19. The system as recited in claim 18, wherein the system includes a plurality of available gingival healing cuffs, each with a different size or configuration, wherein each cuff includes a hollow opening at a center portion of the gingival healing cuff, for receipt of the tri-lobe exterior structure for receipt of the tri-lobe exterior structure of the omni-abutment, wherein the hollow opening in each gingival healing cuff is identically sized or differently sized.

20. The system as recited in claim 18, further comprising at least one of a buccal or lingual handle portion extending from the gingival healing cuff.

21. A system including the omni-abutment as recited in claim 5, for use with a dental implant, wherein the system further includes a scanning body insert, impression post insert, torque wrench insert, percussion insert, or other insert, which insert couples directly into a dental implant underlying the omni-abutment.

\*    \*    \*    \*    \*